(12) United States Patent
Grahn et al.

(10) Patent No.: US 7,947,008 B2
(45) Date of Patent: May 24, 2011

(54) SHUNT AND METHOD TREATMENT OF GLAUCOMA

(75) Inventors: Bruce Harold Grahn, Saskatoon (CA); Eric Shad Storey, Baton Rouge, LA (US); Denise Sharon Stilling, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 324 days.

(21) Appl. No.: 12/190,211

(22) Filed: Aug. 12, 2008

(65) Prior Publication Data
US 2009/0036818 A1 Feb. 5, 2009

Related U.S. Application Data

(63) Continuation of application No. 10/515,999, filed as application No. PCT/CA03/00774 on May 29, 2003, now abandoned.

(60) Provisional application No. 60/383,599, filed on May 29, 2002.

(51) Int. Cl.
*A61M 1/36* (2006.01)

(52) U.S. Cl. ................................. 604/9; 604/8

(58) Field of Classification Search ................ 604/7–10, 604/27, 28, 30, 264, 521, 289; 606/153
See application file for complete search history.

(56) References Cited

U.S. PATENT DOCUMENTS

| | | |
|---|---|---|
| 3,788,327 A | 1/1974 | Donowitz et al. |
| 4,037,604 A | 7/1977 | Newkirk |
| 4,402,681 A | 9/1983 | Haas et al. |
| 4,554,918 A | 11/1985 | White |
| 4,604,087 A | 8/1986 | Joseph |
| 5,127,901 A | 7/1992 | Odrich |
| 5,326,345 A | 7/1994 | Price, Jr. |
| 5,338,291 A | 8/1994 | Speckman et al. |

(Continued)

FOREIGN PATENT DOCUMENTS

EP 0228185 7/1987

(Continued)

OTHER PUBLICATIONS

Cullen C. et al., "Anterior chamber to frontal sinus shunt for the diversion of aqueous humour: A pilot study in four normal dogs," Veterinary Ophthalmology 1(1):31-39, 1998.

(Continued)

*Primary Examiner* — Leslie R Deak
(74) *Attorney, Agent, or Firm* — Greenlee Sullivan PC

(57) ABSTRACT

This invention provides a shunt for implantation between the anterior chamber of the eye and the epithelial-lined space through the frontal sinus bone of a patient for the treatment of glaucoma. The shunt includes a tube having a length sufficient to span the distance between the anterior chamber of the eye and the epithelial-lined space of the patient, the tube having an open anterior chamber end and a closed epithelial-lined space end, and a seal device associated with the tube between the anterior chamber and epithelial-lined space ends, for sealing a hole in the frontal sinus bone, and for anchoring the tube against movement from the frontal sinus bone. The shunt also includes a fluid pressure openable valve in the tube, located at or near the epithelial-lined space sinus end, allowing for controlled flow of aqueous humor through the tube when implanted. The invention also extends to a method of treating glaucoma in a patient by surgically implanting the shunt between the anterior chamber of the eye and the frontal sinus.

27 Claims, 7 Drawing Sheets

U.S. PATENT DOCUMENTS

| | | | |
|---|---|---|---|
| 5,346,464 A * | 9/1994 | Camras | 604/9 |
| D356,867 S | 3/1995 | Krupin | |
| 5,454,796 A | 10/1995 | Krupin | |
| 5,810,761 A | 9/1998 | Saens-Arrollo | |
| 6,007,510 A | 12/1999 | Nigam | |
| 6,142,969 A | 11/2000 | Nigam | |
| 6,283,934 B1 | 9/2001 | Borgesen | |
| 6,454,794 B1 | 9/2002 | Knudson et al. | |
| 6,510,600 B2 | 1/2003 | Yaron et al. | |
| 6,666,841 B2 | 12/2003 | Gharib et al. | |
| 2002/0156413 A1 | 10/2002 | Williams et al. | |
| 2003/0055372 A1 | 3/2003 | Lynch et al. | |
| 2003/0135149 A1 | 7/2003 | Cullen et al. | |

FOREIGN PATENT DOCUMENTS

| | | |
|---|---|---|
| WO | WO 00/64389 | 11/2000 |

OTHER PUBLICATIONS

Grahn B. H. et al., "Frontal sinus shunting of aqueous humor in dogs with primary glaucoma," American College of Veterinary Ophthalmologists, 30th meeting, Chicago, Illinois, Nov. 3-7, 1999.

Storey E. S. et al., "Application of valved anterior chamber to frontal sinus shunts in dogs with glaucoma," American College of Veterminary Ophthalmologists, 32$^{nd}$ annual meeting, Sarasota, Florida, Oct. 9-13, 2001.

Cullen C.L., "Preliminary findings of a canine frontal sinus valved glaucoma shunt," American College of Veterinary Ophthalmologists, 32$^{nd}$ annual meeting, Sarasota, Florida, Oct. 9-13, 2001.

Article: "Eye implant for glaucoma," JAMA 243(7):624, 1980.

Gelatt K. N. et al., "evaluation of the Krupin-Denver valve implant in normotensive and glaucomatous beagles," JAVA 191(11), Dec. 1, 1987.

Dohlman C.H. et al., "Can a glaucoma shunt tube be safely extended to the lacrimal sac or the ethmoid sinus in keratoprothesis patients?" Digital Journal of Opthamology 7(3), 2001.

Gal M. R., "A novel glaucoma drainage valve," Master of Applied Science Thesis, Department of Mechanical Engineering, Institute of Biomedical and Biomaterials Engineering, University of Toronto, 1999.

Francis B. A. et al., "Characteristics of glaucoma drainage implants during dynamic and steady-state flow conditions," Ophthalmology 105(9):1708-1714, 1998.

Moffett D. et al., "Human Physiology Foundations & Frontiers," 2$^{nd}$ edition, Mosby-Year Book, Inc., St. Louis, Missouri, 1993, pp. 268-271.

Prate, Jr. J. A. et al., "In vitro and in vivo flow characteristics of glaucoma drainage implants," Ophthalmology 102(6):894-904, 1995.

International Search Report, International Application No. PCT/CA03/00774, Nov. 12, 2003, 4 pages.

* cited by examiner

SHUNT AND METHOD TREATMENT OF GLAUCOMA

CROSS-REFERENCE TO RELATED APPLICATIONS

This application is a continuation of U.S. patent application Ser. No. 10/515,999, with official filing date of Apr. 14, 2005, which is the national stage of PCT International Application No. PCT/CA03/00774, filed May 29, 2003, which claims the benefit of U.S. patent application No. 60/383,599, filed May 29, 2002. Each of these applications is incorporated herein by reference in entirety.

FIELD OF INVENTION

The present invention relates to a method and device for controlling aqueous humor flow from the anterior chamber of the eye in the treatment of glaucoma.

BACKGROUND OF THE INVENTION

Glaucoma is a medical condition in which the intraocular pressure of the eye increases. The anterior chamber, the cavity located between the cornea and lens, is filled with a fluid called aqueous humor. The aqueous humor drains from the anterior chamber to the venous system through the canals of Schlemm and is replaced continuously by secretions from the ciliary body. Glaucoma occurs when aqueous humor does not drain properly from the anterior chamber, causing an increase in intraocular pressure, closure of surrounding blood vessels, and damage to the retina and optic nerve. This condition, left untreated, can be very painful and lead to blindness. It is estimated that 65 million people world-wide suffer from this condition (Glaucoma Research Foundation, 2002). Animals can also be affected by this condition. It is estimated there are 65 million dogs in North America, of which approximately 1.3 million will develop glaucoma.

Closed-angle glaucoma occurs when the iris becomes misshapen and blocks the canals of Schlemm. The underlying cause of open-angle glaucoma is a blockage within the canals. About 3 million people in the United States are afflicted with open-angle glaucoma (Glaucoma Research Foundation, 2002). Secondary glaucoma, either open- or closed-angle, can be caused by injury, abnormal structures, inflammation, tumours, certain drugs, or diseases (Moffett et al, 1993).

Current treatments consist of medications, laser surgery and implantable drainage devices (Glaucoma Research Foundation, 2002). Medications, often in the form of eye drops, work to decrease intraocular fluid production, increase fluid drainage, or both. These medications are associated with side effects, including burning sensations in the eye, headaches, cardiac fluctuations and blurred vision. The administration of medications for the treatment of animals is difficult and ineffective. Laser surgery is used to open the fluid draining channels or correct structures in the eye. Multiple surgeries are often required, and medication is normally still used to help control intraocular pressure post-surgery. There is also the risk of allowing too much fluid to drain from the anterior chamber, resulting in hypotony and flattening of the eye.

Implants have also been used in the treatment of glaucoma. These implants drain aqueous humor from the anterior chamber into mesenchymal or subconjunctival tissues surrounding the eye. The aqueous humor of eyes afflicted with glaucoma has a relatively high concentration of cytokines. Cytokines are proteins that mediate the generation of an immune response. Implants that drain aqueous humor into tissues surrounding the eye induce scarring in such tissues, which scarring ultimately inhibits absorption of fluid from the shunt. Consequently glaucoma recrudesces and visual impairment redevelops.

Current drainage implants are classified as either restrictive or non-restrictive flow devices (Gal, 1999). Non-restrictive flow devices, such as the Molteno drainage implant, rely on the formation of fibrous tissue to slow the drainage of fluid from the eye. These implants require at least two invasive surgical procedures. The initial surgery is required to implant the device. Fibrous tissue generally takes several weeks to form, making it necessary to clamp or tie the device to limit fluid drainage and prevent hypotony. A second surgery is required to unclamp or untie the device once fibrosis has occurred. Restrictive flow devices, such as the Krupin Eye Disk, are designed with components that respond to fluid pressure, see for example U.S. Pat. No. 5,454,796, issued Oct. 3, 1995 to Krupin, and U.S. Design Pat. No. Des. 356,867 issued Mar. 28, 1995 to Krupin. When pressure in the drainage tube exceeds a certain limit, the component, or valve, will open and allow fluid to drain. Several problems have occurred with these devices. First, it is difficult to calibrate the valve to maintain an optimal intraocular pressure, and often leads to hypotony. Second, the formation of fibrous tissue can occlude the valve and render the drainage device useless. A similar restrictive flow device is disclosed in U.S. Pat. Nos. 6,142,969 and 6,007,510, issued to Nigam.

The frontal sinus 16 is an epithelium-lined cavity which is not affected by cytokines. Studies by Cullen et al., with a shunt implanted in dogs between the anterior chamber and the frontal sinus showed no evidence of bacterial movement from the frontal sinus 16 to the eye through this device (see Cullen et al, 1998).

Although somewhat successful in less severe cases, the prior art implant devices, while successful in the short term, are not effective for long-term management of glaucoma due to occurrence of hypotony or more difficult forms of glaucoma. More effective treatment regimes are needed.

SUMMARY OF INVENTION

To overcome the difficulties induced by fibrosis blocking the valve or drainage tube and the scarring invoked by the cytokine response, the inventors have developed a shunt device and method of treatment for glaucoma that diverts aqueous humor from the anterior chamber to an epithelial-lined space. While the method and device have been successfully demonstrated with dogs, in which the shunt was implanted between the anterior chamber of the eye and the frontal sinus, the invention has application for the treatment of glaucoma in all species of animals, including humans, and to other epithelial-lined spaces besides the frontal sinus.

The term "epithelial-lined space", as used herein and in the claims includes epithelial and epithelial-lined spaces, including the frontal sinus, maxillary sinus, nasal sinus, other respiratory sinuses or spaces, subdural space, and meningeal cavity.

Broadly, the invention provides a shunt for implantation between the anterior chamber of the eye and the epithelial-lined space through the frontal sinus bone of a patient for the treatment of glaucoma. The shunt includes a tube having a length sufficient to span the distance between the anterior chamber of the eye and the epithelial-lined space of the patient, the tube having an open anterior chamber end and a closed epithelial-lined space end, and a seal device associated with the tube between the anterior chamber and epithelial-lined space ends, for sealing a hole in the frontal sinus bone, and for anchoring the tube against movement from the frontal sinus bone. The shunt also includes a fluid pressure openable valve in the tube, located at or near the epithelial-lined space sinus end, allowing for controlled flow of aqueous humor through the tube when implanted.

The invention also broadly provides a method of treating glaucoma in a patient, comprising (a) forming a hole from the exterior into the epithelial-lined space, for example in the frontal sinus bone, of the patient; (b) surgically implanting through the hole, between the anterior chamber and the epithelial-lined space, a shunt having a fluid pressure openable valve; and (c) draining aqueous humor from the anterior chamber through the shunt to the epithelial-lined space. The shunt preferably includes a tube having an open anterior chamber end and a closed epithelial-lined space end, and wherein the valve is located at the frontal sinus end, allowing for controlled flow of aqueous humor through the tube when implanted.

BRIEF DESCRIPTION OF THE PREFERRED EMBODIMENTS

The shunt of the present invention, shown generally at 10 in the Figures is shown as designed for implantation between the anterior chamber and the frontal sinus, however, the shunt has application for implantation to other epithelial-lined spaces, including the maxillary sinus, nasal sinus, other respiratory sinuses or spaces, subdural space, and meningeal cavity.

Figure 1:
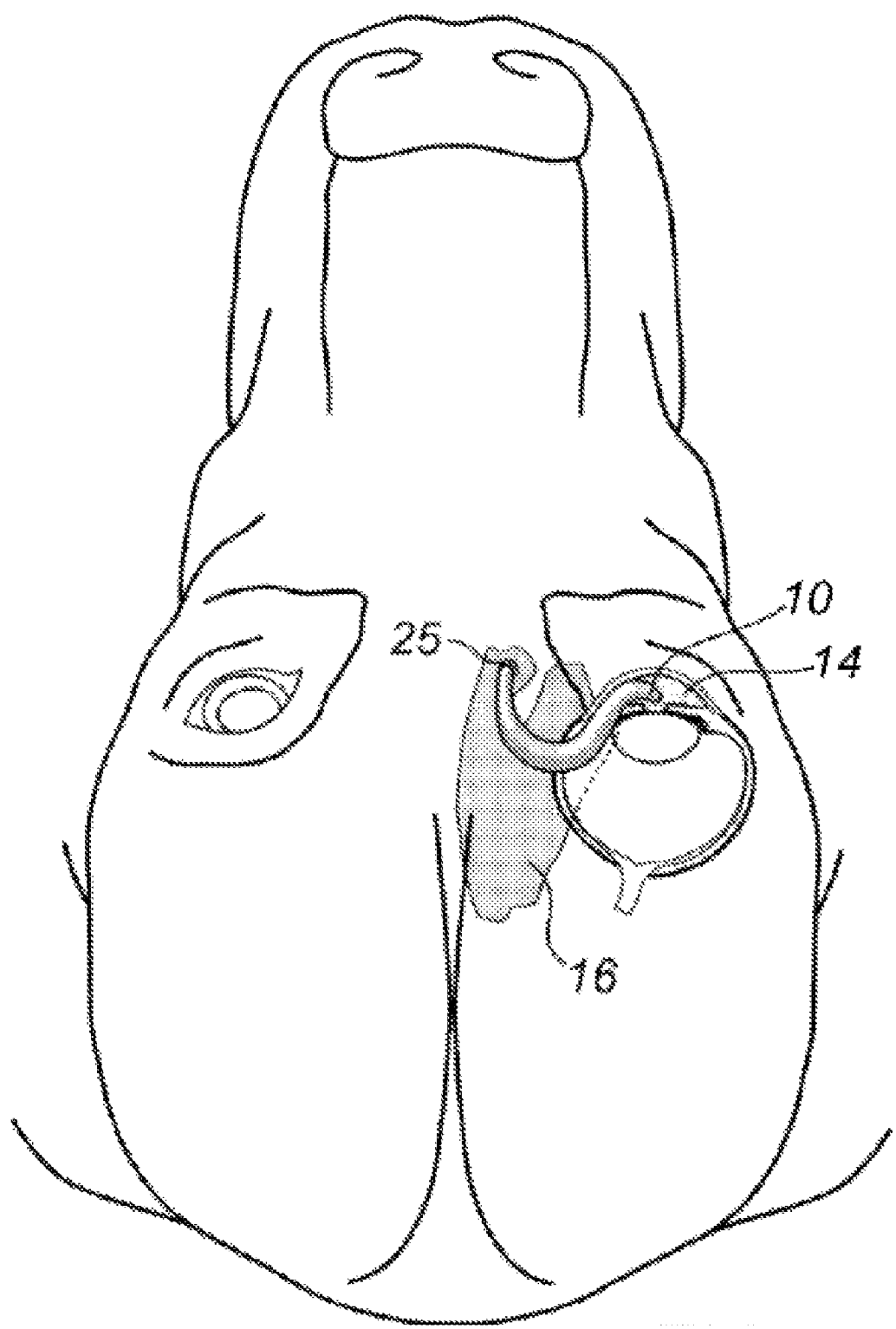
FIG. 1 illustrates the shunt of the present invention implanted in a dog, with portions of the eye being cut away to illustrate placement of the shunt between the anterior chamber and the frontal sinus.
Figure 2:
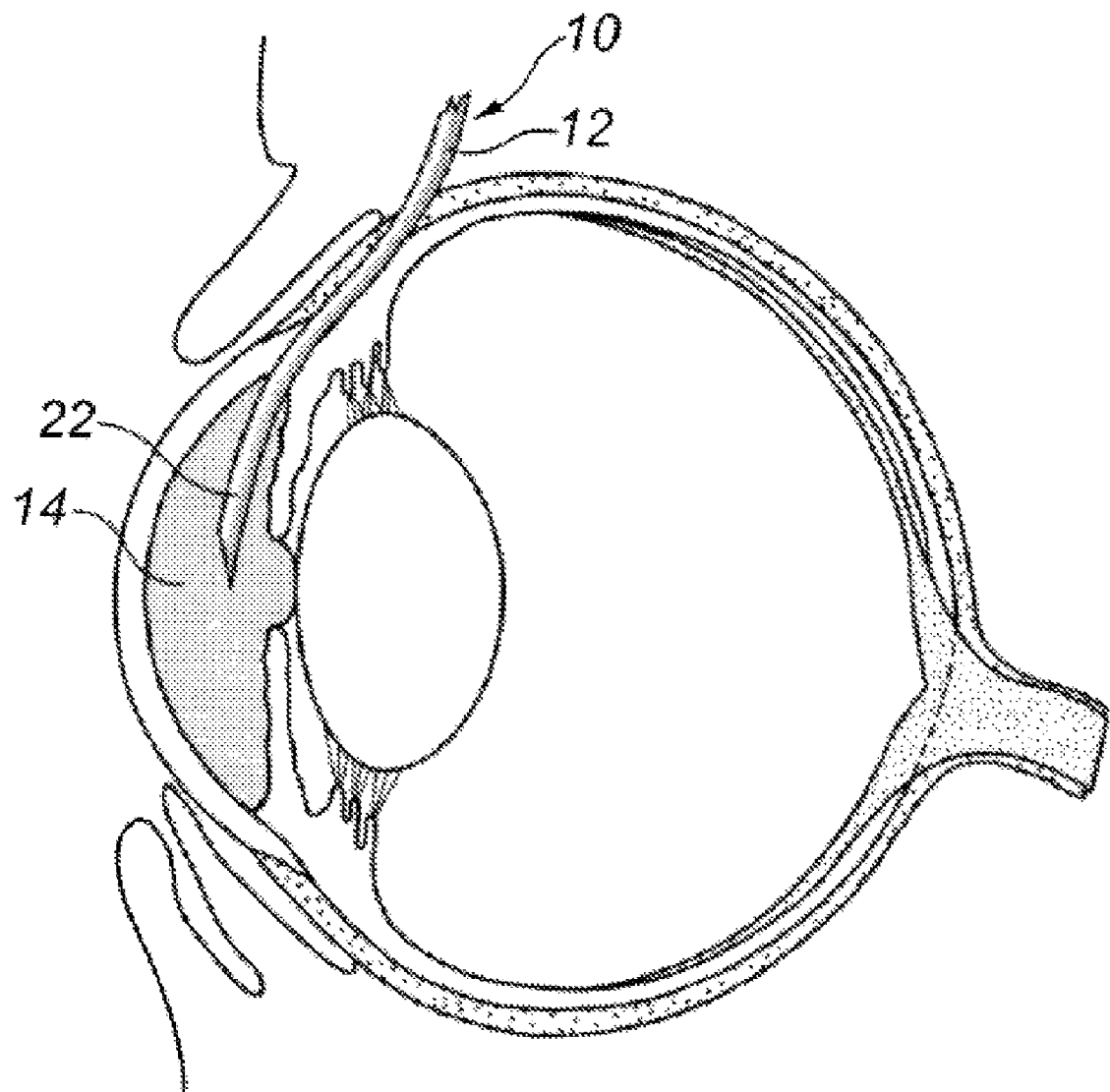
FIG. 2 is a sectional view of the shunt implanted in the eye, better illustrating the anterior chamber placement.
Figure 3:
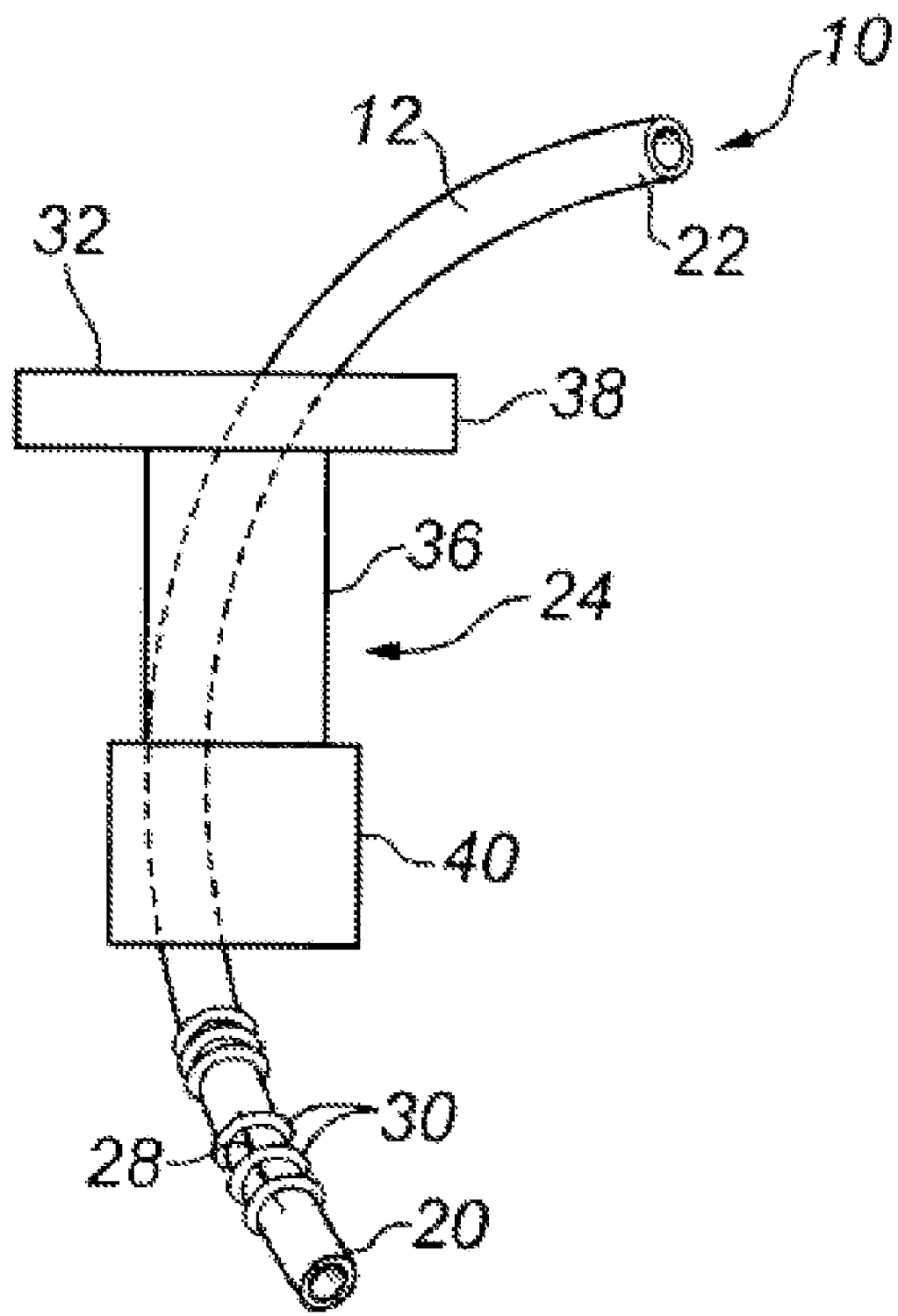
FIG. 3 is a sectional view of the shunt threaded through the anchoring sealing device.
Figure 4:
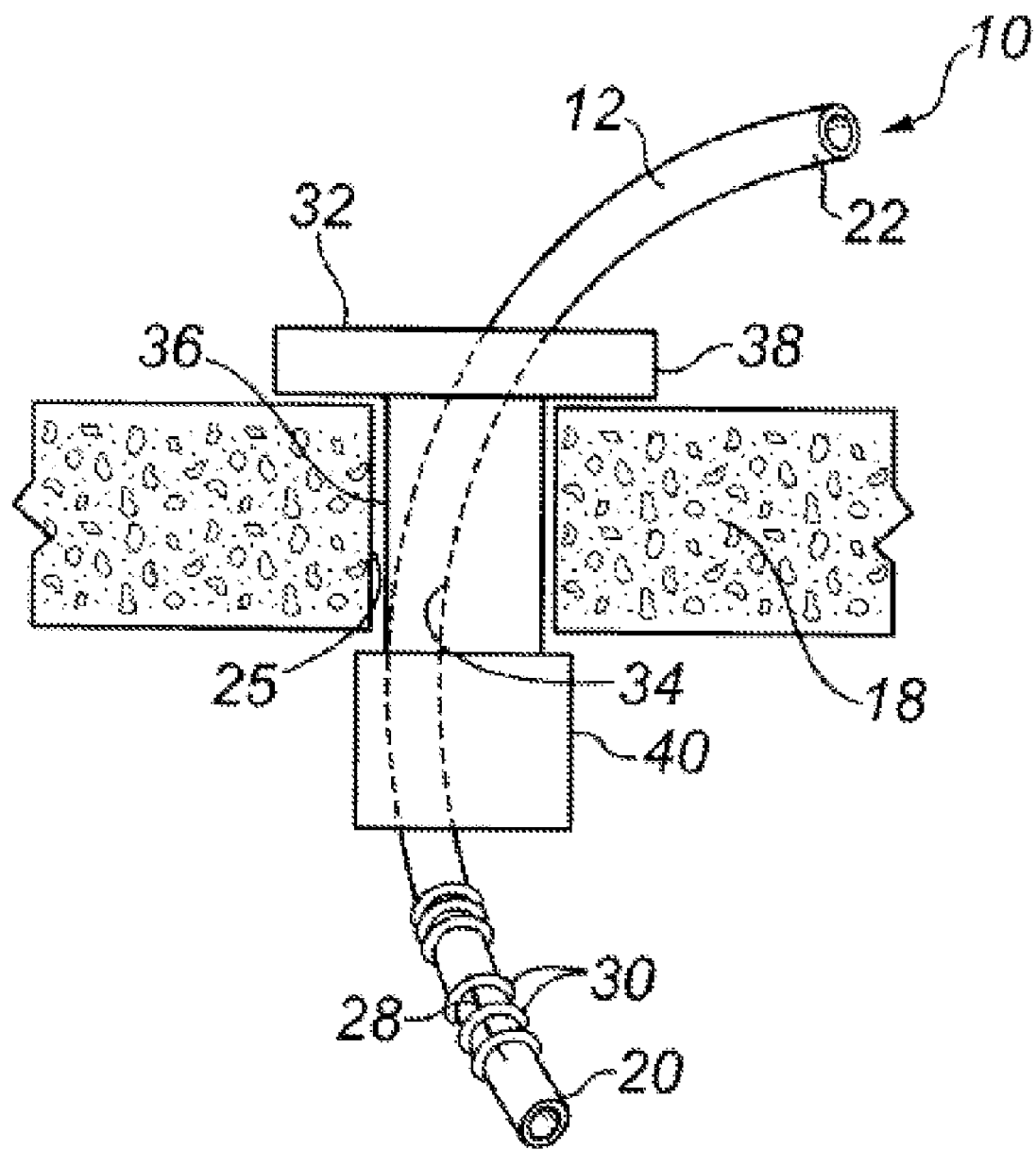
FIG. 4 is a sectional view of the shunt showing the anchoring sealing device in place in the hole in the frontal sinus bone.
Figure 5:
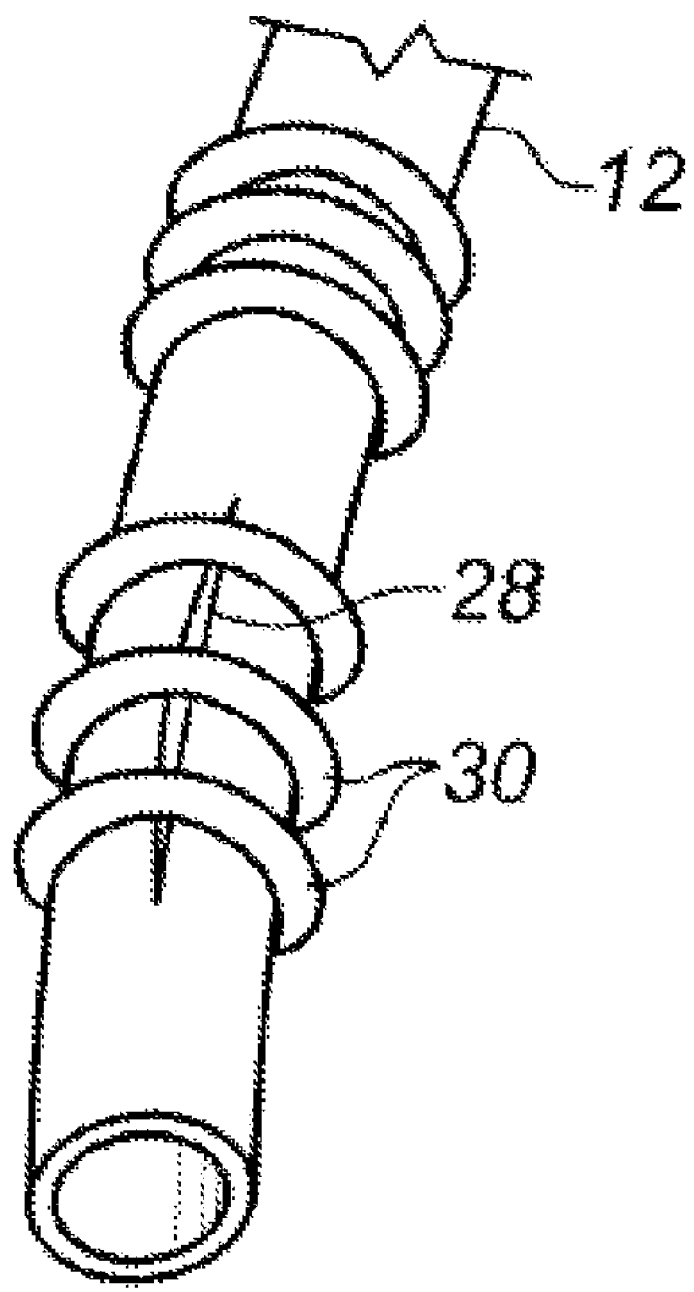
FIG. 5 is a partial perspective view of the shunt showing the slit valve and the ligatures used to adjust and control flow of aqueous humor through the valve.

The details of a first embodiment of the shunt 10 are best shown in FIGS. 3-5, while the placement of the shunt 10 in a dog is shown in FIGS. 1 and 2. The shunt 10 consists of a tube 12, made of a biocompatible material such as silicone. The length of the tube required is dependent on the species, but is of sufficient length to reach the distance between the anterior chamber 14 and the frontal sinus 16, through the frontal sinus bone 18, of the given animal species. The tube 12 thus has a frontal sinus end 20 and an anterior chamber end 22. The tube 12 is threaded through a sutureless sealing device 24, which seals around the hole 25 in the frontal sinus bone 18. The sealing device 24 is located close to the frontal sinus end 20 of the tube 12. This acts to hold the tube 12 in place as well as prevents it from kinking. A valve device 26 is provided at or near the frontal sinus end 20 of the tube 12 (i.e., when implanted the valve is on the sinus side of the frontal sinus bone). The sealing device 24 also functions to prevent serum and clots from exuding from the exposed bone 18 and from subcutaneous tissues within the frontal sinus and into the valve device 26. In FIGS. 1 and 3, the valve device 26 is shown to be of a slit valve type, formed by constructing a slit 28 in the frontal sinus end 20 of the tube 12 approximately parallel to the longitudinal axis of the tube 12. This frontal sinus end 20 is inserted into the frontal sinus 16 and held in place with the sealing component 24, which straddles the frontal sinus bone 18 and anchors the tube against movement in either direction. The tube 12 is then tunnelled subcutaneously towards the eye and into the anterior chamber 14. Surgical implantation of the shunt 10 is more fully explained below.

The shunt will generally have a length ranging from 30 to 150 mm, and may be trimmed to length during surgery. However, the shunt can be made to fit any species of animal (including humans) by trimming any excess length from the anterior chamber end 22. The shunt is generally formed from flexible, biocompatible materials such as silicone, glass, medical grade acrylics, plastic, or metal manufactured parts, with silicone or any similar biocompatible, flexible material being most preferred. One advantage of the present invention is that the tube 12 of the shunt 10 can be formed from tubing having internal and external diameters that can be varied according to the patient species together with the surgeon's preference and/or the surgeon's skill. The dimensions are affected by the space available in a particular patient's eye between the cornea and the lens. The tube 12 should be sized so as to be fitted into such space in such a fashion that the anterior chamber end 22 does not contact the iris, lens or cornea. While not being limiting, exemplary dimensions for the shunt of the present invention for implantation in dogs, taking into account the ordinary skill of a surgeon, are as follows. For the tube portion 12, flexible tubing (such as silastic tubing) ranging from 0.25 to 0.64 mm inner diameters and 0.6 to 0.14 mm outer diameters with a wall thickness from 0.2 to 0.64 mm are optimal.

The method and shunt 10 of the present invention allows for the control of aqueous humor flow from the valve device 26 by means of a simple adjustment procedure, explained more fully below. A major constraint of prior art glaucoma shunts, the control of intraocular pressure via fluid flow from valves, is addressed with the present invention in that the flow of aqueous humor is controlled by using an adjustable valve, or by associating a flow control device with a valve. As best shown in FIG. 5, flow adjustment through the slit 28 is provided by means of one or more ligature devices 30. The ligature devices 30 may be formed from O-rings, D-rings, C-clamps, sutures, or circumferential sutures formed of a biocompatible material, which are placed or tied around the tube 12 over and/or adjacent the slit 28. These ligature devices 30 tighten the slit 28, allowing less fluid to escape from the tube 12 and drain from the anterior chamber 14. The addition or removal of these ligature devices 30 to control flow can be made by a simple skin incision above the frontal sinus 16, which also allows for easy removal of the shunt 10 (more fully described below). Hydrostatic pressures of aqueous humor of glaucoma-affected patients can vary among species and idiotypically among patients. Also, rates of aqueous fluid of different species vary significantly. The easy adjustment of the valve device 26 allows this shunt 10 to be used in the treatment of various species, as well as each individual within a species.

The slit 28 will generally be about 0.5 to 2.0 mm long, and oriented approximately parallel to the longitudinal axis of the tube 12. The slit 28 is preferably perpendicular to the tangent of the tube wall. Variability in the length of the slit, the number of slits, the number of ligature devices and the positioning of ligature devices in relation to the slit provides flexibility sufficient to permit adjustment for use with various species, as well as various hydrostatic pressures of aqueous humor.

As shown in FIG. 5, the ligature devices 30 around the tube 12, are mounted circumferentially around the longitudinal axis of the slit 28 and snug enough to slightly indent the tube 12 without disturbing the orientation of the slit. The ligature devices 30 are formed of a biocompatible material, with metal C-shaped clamps, and plastic, silicone, or rubber round O-rings, being most preferred. These preferred ligature devices are less prone to surgeon error than sutures in that they can be sized such that they do not excessively compress the valve walls and can be pre-placed at one or both ends of the slit 28. During surgical placement, these ligature devices 30 are slidably moved into variable positions along the length of the slit 28, and the intraocular pressure (fluid pressure indicative of glaucoma operative to open valve) is measured to ensure a desired intraocular pressure will open the valve device 26. Multiple ligature devices, up to 3/mm, have been found to provide flexibility that allows the surgeon to finely adjust valve tension and aqueous flow rates through the valve device 26.

Figure 7:
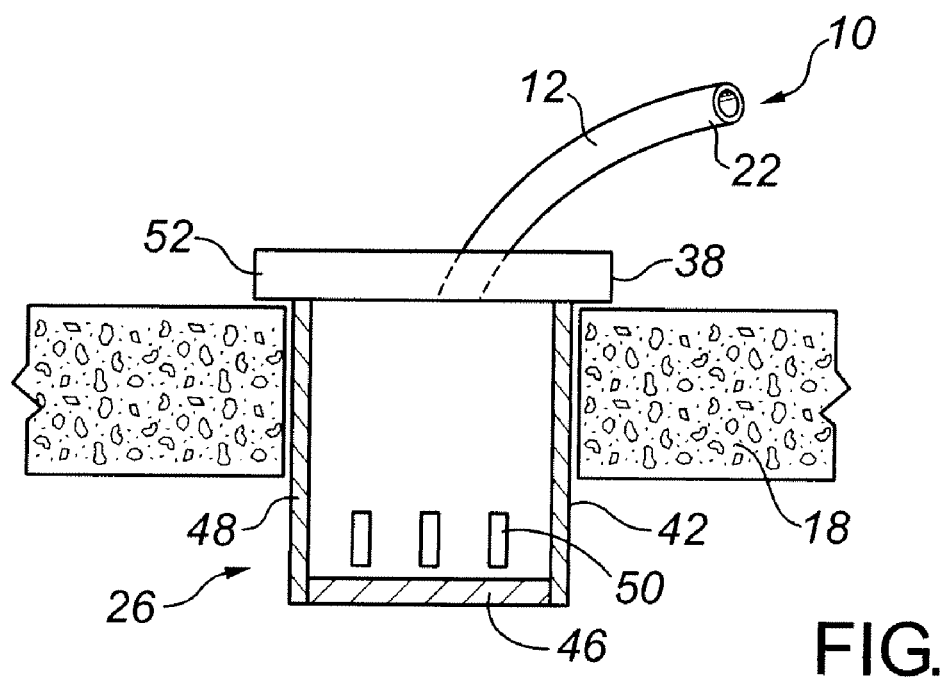
FIG. 7 is a schematic side sectional view of a third embodiment of a shunt of the present invention, illustrating a drainage reservoir for housing alternate valve devices, which drainage reservoir also functions as the sealing device.
Figure 8:
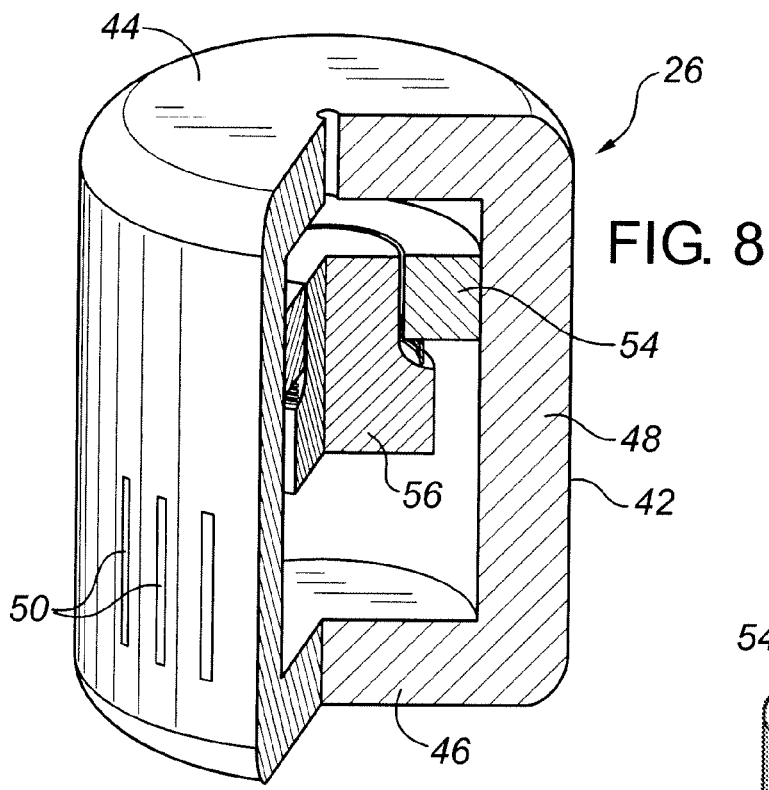
FIG. 8 is a perspective view, partially cut-away, showing a tapered nipple plug type valve within the reservoir chamber of either FIGS. 7 and 8.

The sealing device 24 can take a variety of forms, such as a widened portion (not shown) of the tube 12, a widened reservoir plug as shown in FIG. 7, or a spool-shaped plug type seal as shown in FIGS. 3 and 4. It is functional to seal the shunt 10 against the hole 25 in the frontal sinus bone 18, and to anchor the shunt against movement relative to the bone 18 once implanted. The sealing device also bends the tube 12 though an angle sufficient to ensure that the valve device 26, when the shunt 10 is implanted, is wholly within the frontal sinus and maintained in the space (not abutting the frontal sinus epithelium. For most species of patients, an bending angle of 80 to 100° is desired, so as to maintain the most desired ingress and egress angle of the shunt between the frontal sinus 16 and the anterior chamber 14. This best positions the shunt 10 and avoids narrowing of the lumen of the tube 12 or kinking of the tube 12. In one embodiment designed for dogs, an angle of about 90° was used.

The sealing device is most preferably a molded, spool-shaped (grommet-like) plug 32, attached to the tube 12 and having an central bore 34 sized to fit snugly around the tube 12. The plug may be manufactured by carving a wax or wooden mold, positioning the tube 12 in the mold at the desired ingress and egress angles, flooding the mold with liquid silicone, allowing it to set and removing the plug from the mold. The plug 32 has a central portion 36 joined to and an upper flange or lip (anterior chamber facing) 38 and a lower flange or lip (frontal sinus facing) 40. The flanges 38, 40 have a widened diameter relative to the diameter of the central portion 36. Biocompatible materials for the plug are silicone (a preferred embodiment) and rubber, plastic, glass, or metal components. At least the lower flange 40, which is frontal sinus facing, is made of a viscoelastic material such as silicone, to enable it to be compressed and forced through the hole 25 in the sinus bone 18. As mentioned above, the plug 32 bends the tube 12 though about an 80 to 100° angle.

The shunt 10 should enter the anterior chamber 10-25 degrees anterior to the limbal plane to avoid contact with the iris, crystalline lens, or corneal endothelium. The trephine hole 25 of the frontal sinus 16 is best situated approximately perpendicular to the frontal bone 18. The tube 12 should enter and leave the at plug 32 at about 90° (i.e., bend the tube through about 90°), but curve gently within the central bore 34 of the plug 32, to decrease the potential for occlusion of the shunt 10 by kinking the tube 12 or allowing trapping of fibrin clots within this turn of the tube 12. The frontal sinus plug 32 should be compressible to allow the lower flange 40, having a diameter slightly larger than the trephined hole 25, to be introduced into the frontal sinus (preventing unintentional egression of the shunt 10), and providing pressure against the bony walls of the trephined hole 25 to stop hemorrhage from the bone 18 and to stop fibrin and blood from collecting around the valve device 26.

Without being limiting, in one embodiment of the shunt designed for dogs, the center portion 36 has a diameter of about 0.25-1.5 mm, which is approximately equal to the bore dimensions of the trephined hole 25, and approximately 0.1 mm shorter than the thickness of the bone 18 (1-2.5 mm), to create a tight sealing fit to prevent haemorrhage from the bone 18 that may drain onto the valve device 26. The external diameter of the flanges 38, 40 are about 0.1-0.6 mm greater than the outside diameter of the tube 12, and at least twice the diameter of the trephined hole 25 to prevent complete ingress into the frontal sinus 16.

As indicated above, the shunt of the present invention, and its parts, are formed from biocompatible materials, that is materials which are biologically non-reactive and non-toxic to the patient. Examples are silicone (sialastic tubing), glass, medical grade plastic and some metals.

Figure 6:
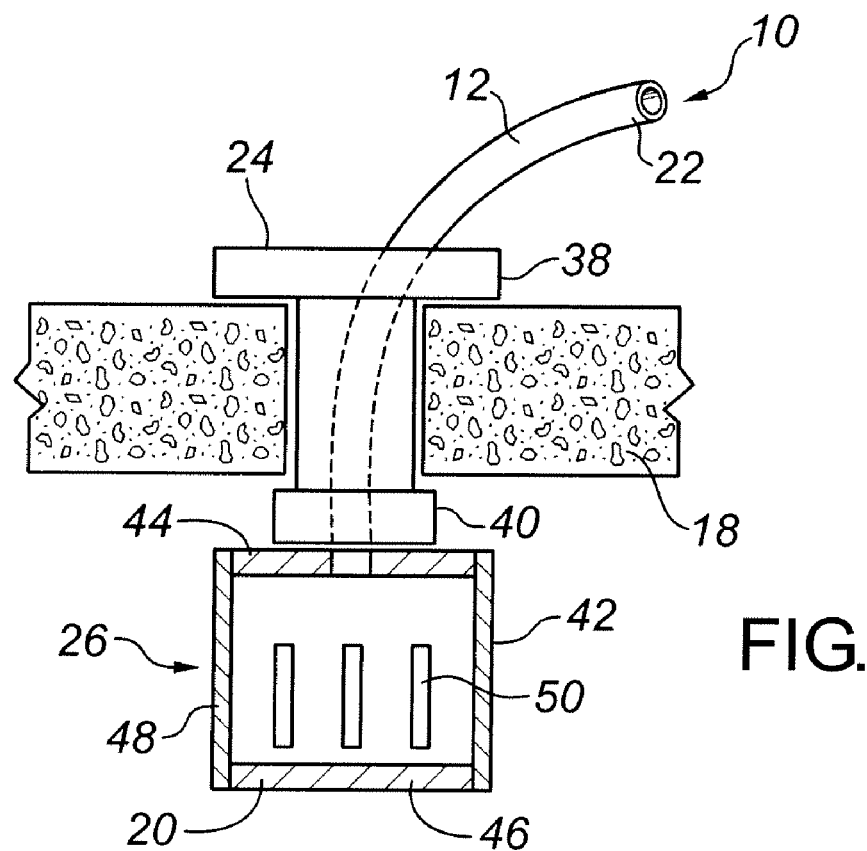
FIG. 6 is a schematic side sectional view of a second embodiment of a shunt of the present invention, illustrating a drainage reservoir housing for alternate valve devices.
Figure 10:
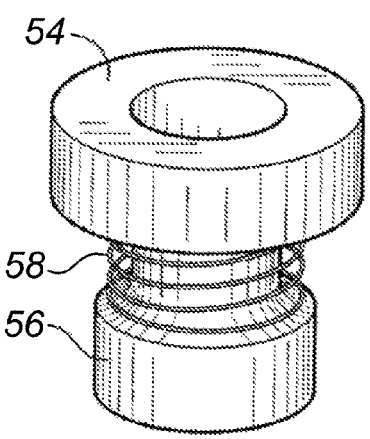
FIG. 10 is a perspective view of the taper nipple plug valve unit of FIGS. 8 and 9.
Figure 9:
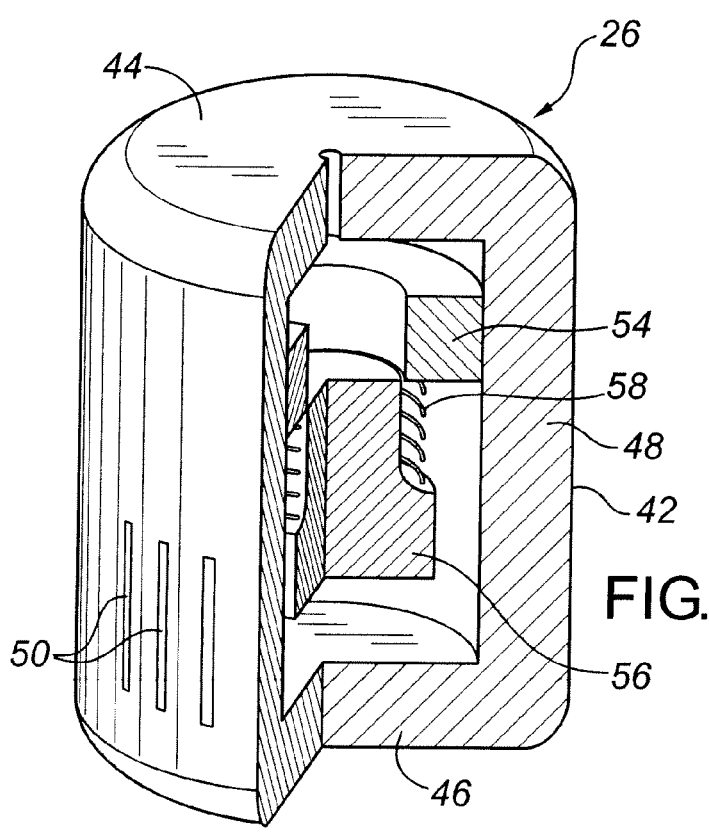
FIG. 9 is a perspective view, partially cut-away, showing the tapered nipple plug valve of FIG. 8 in the open position.

Second and third embodiments of the shunt 10 are shown in FIGS. 6-10. In FIG. 6, the valve device 26 is shown to include a drainage reservoir 42 housing a valve element (not shown). In FIG. 7, the drainage reservoir 42 is shown to also function as the sealing device 24 in the frontal bone 18. A variety of check valve types may be incorporated in these embodiments, such as the nipple plug type valve shown in FIGS. 7-10, or a butterfly valve (not shown). The reservoir 42 is shown in the figures to be formed from an apertured upper plate 44, a closed bottom plate 46, connected together by a side wall 48 which includes perforations such as longitudinal slits 50 which allow fluid to drain from the reservoir 42. In FIG. 7, the reservoir 42 is shown to include a widened sealing flange 52, to seal and anchor against the frontal sinus bone 18. The nipple plug type valve components are best shown in FIG. 10, to include an upper orifice plate 54 and a lower nipple plug 56 operative to seal in the orifice plate 54. The plate 54 and plug 56 are joined together in a normally closed position (shown in FIG. 8), by a spring member 58, having a tension such that the valve is fluid openable under predetermined pressures associated with glaucoma to allow fluid to flow through the orifice plate 54 and out the perforations 50. When implanted, once the pressure diminishes the nippled plug 56 will reseal against the orifice plate 54.

Method of Treatment of Glaucoma—Surgical Implantation and Testing

Surgical implantation of the shunt 10 in accordance with the present invention is described below, following aseptic preparation of the surgical field including the eye and skin of the patient and positioning the patient under an operating microscope. Over the ipsilateral frontal bone, the skin, subcutaneous tissues, and muscle over the zygomatic process of the frontal bone are incised. The incision should be long enough to expose the frontal bone over the frontal sinus (typically approx 1" long and oriented rostrocaudally. The location of the frontal sinus 16 can be confirmed by tapping the frontal bone of the zygomatic process with a solid object (such as a surgical instrument) to confirm a hollow sound.

A drilling device (such as a Jacob's chuck and Steinmann's pin—not shown), sized appropriately for the patient, is employed to make the hole 25 in the bone 18 over the frontal sinus 16, into the frontal sinus 16 from the exterior. The size of the hole 25 will vary with patient and species, and is matched to the size of the sealing device 24. The sinus is visualized as a white cavity.

Patency of the shunt 10 is confirmed by (i) cannulating the shunt (anterior chamber end 22) with a aqueous-fluid-filled syringe and needle (typically 27-30 ga.) assembly—not shown; (ii) flushing the aqueous fluid (e.g. sterile balanced slat solution) through the shunt 10 under pressure from the syringe; and (iii) visualizing fluid passing through the valve device 26.

The frontal sinus end 20 of the shunt 10 is placed within the trephined hole 25 of the sinus and can be held in place by slight compression of the sealing device 24 and by the upper and lower flanges 38, 40.

An eyelid speculum, not shown, is then placed ipsilaterally on the eyelids to expose the conjunctival surface. A conjunctival incision is made from the limbus (junction of cornea, schlera, and conjuctiva) to the formix (reflexion of the conjuctiva under the eyelid) and extended through to the epischlera.

An instrument such as pair of small forceps, not shown, is used to bluntly dissect a tunnel from the conjunctival incision to the frontal sinus incision (typically over the dorsal rim of the orbit to the original surgical dissection exposing the frontal sinus). When the tip of such instrument can be visualized it can be used to grasp the free end (anterior chamber end 22) of the shunt. The shunt 10 is then drawn back through the tunnel through the conjunctival incision. The shunt 10 is layered across the surface of the cornea and the length of the shunt is trimmed so as to adjust its length such that is rests approximately ¼ of the vertical length of the anterior chamber 14. The anterior chamber end 22 of the shunt is trimmed obliquely at 45 to 60 degrees with the bevel opening anteriorly.

A cutting device (e.g., 20 gauge disposable stilleto blade, not shown) is used to enter the anterior chamber 14 at the limbus. The angle at which the blade enters the anterior chamber should be approximately 20° (the shunt 10 should enter the anterior chamber 14 at 10-25° anterior to the limbal plane to ensure that the shunt is positioned equal distance between the iris and the cornea to avoid contact between the shunt and the iris, crystal lens, or corneal endothelium).

Small forceps (e.g. tying forceps) are used to grasp the anterior chamber end 22 of the shunt near the bevelled end, and the shunt 10 is inserted into the anterior chamber 14. The shunt 10 is anchored to the sclera with, for example, nonabsorbable (monofilament) more than one (usually to or maximally (practically) three) sutures in a simple interrupted pattern.

The Tenon's capsule and conjunctiva are closed with, for example, simple interrupted sutures of small (7-0 to 10-0) monofilament absorbable sutures. The frontal sinus end 20 of the shunt is withdrawn from the frontal sinus 16 and monitored for flow of aqueous humor through the valve device 26. When fluid flow through the valve device 26 is confirmed, such flow is adjusted at the valve device 26. In the case of a slit valve, the flow is adjusted with at least one ligature device 30 around or adjacent the slit 28 to maintain a desired intraocular pressure, which can be measured at the corneal surface with an applanation tonometer in the O.R. (normal for dog approximately 18 mm Hg). The valve device 26 is adjusted to open above this predetermined and known fluid pressure associated with glaucoma. The predetermined fluid pressure associated with glaucoma is known for other species, and the valve device can be adjusted accordingly for other species.

The frontal sinus end 20 of the shunt 10 is then replaced into the frontal sinus 16.

Subcutaneous tissues are closed with, for example, small (3-0 to 6-0) monofilament absorbable sutures in a simple continuous pattern. The skin is subsequently closed with, for example, small (3-0 to 5-0) monofilament nonabsorbable suture in a simple interrupted pattern.

It is common with all intraocular shunts to become fibrin coated or occluded with fibrin shortly after surgery (within the first week post-surgery). The shunt 10 of this invention can be flushed through the valve device 26 by incising the skin, removing the frontal sinus end 20, and back flushing an antifibrinolytic compound (e.g. tissue plasminogen activator (TPA)) retrograde through the shunt. Subsequent flushing of the shunt 10 with TPA or saline in the event of occlusion of the shunt is accomplished by exposing the frontal sinus end 20 of the shunt 10, removing it from the sinus 16, and flushing the shunt retrograde. When flow is observed and the desired intraocular pressure is attained by adjusting the valve device 26, e.g. adjusting the ligature devices 30, the frontal sinus end 20 of the shunt is then replaced, and the surgical site closed as described above.

In the event that the intraocular pressure is observed to be routinely less than the desired intraocular pressure, the frontal sinus end 20 of the shunt 10 can be exposed and ligatures placed at various intervals along the slit 28 to attain the desired intraocular pressure.

EXAMPLE

A shunt of the present invention was designed for and successfully implanted into four dogs having glaucoma. The details of the implanted shunt were as follows:
Tube and Slit Valve
Inner Diameter 0.02" (0.5 mm)
Outer diameter 0.037" (0.94 mm)
Length of Tube (rough cut to be 100 mm) then tailored to each eye in the operating room so that it extended approximately ⅓ away across the anterior chamber of the eye.
Slit—1 mm length
Ligatures—4—to maintain predetermined fluid pressure, adjusted in the operating room
Hole in the Frontal sinus bone (diameter)—(2 mm)
Plug (Sealing Device)
Central Portion (that traversed the width of the bone)—(1.5 mm)
Lower flange—2.5 mm
Upper Flange—5 mm
Length of Plug (Central Portion—traversing the bone)—3 mm These patients did not experience frontal sinus, subcutaneous, conjunctival or intraocular infections; fibrosis, haemorrhage, or other untoward complications. Each of the four patients was reoperated on within days of the first surgery to establish and verify shunt patency and operation and to demonstrate readjustment of the valves and retrograde flushing. Each patient was and is continually to be monitored for visual function and untoward side effects. All anti-glaucoma medications have been discontinued. Regular re-examination with tonometry, visual function testing, biomicroscopy and indirect ophthamoscopy has demonstrated maintenance of vision and desired intraocular pressures for period of up to 2 years post initial surgery.

Advantages

Generally, eyes inflicted with glaucoma build up protein in the aqueous humor. Prior art implanted drainage devices often become blocked with the protein, inhibiting fluid drainage from the eye. To correct this problem with prior art glaucoma treatment devices, an additional invasive surgery is needed to clean, remove, or replace the implant. The method and shunt of the present invention allows the correction to be made by a simple skin incision above the frontal sinus. The sealing device 24 and anterior chamber end 22 of the tube 12 are removed from the frontal sinus 16, flushed with sterile fluid, and reinserted. Further cleanings are not normally required. The fibrous tissue that collects around the shunt once implanted forms a tunnel from the sinus incision to the anterior chamber 14. If the shunt 10 needs to be replaced, the original can be removed through the sinus incision and a new device inserted through the tunnel created by the fibrous tissue. An extensive surgery is not required.

All publications mentioned in this specification are indicative of the level of skill in the art to which this invention pertains. To the extent they are consistent herewith, all publications mentioned in this specification are herein incorporated by reference to the same extent as if each individual publication was specifically and individually indicated to be incorporated by reference. No admission is made that any cited reference constitutes prior art.

Although the foregoing invention has been described in some detail by way of illustration and example, for purposes of clarity and understanding it will be understood that certain changes and modifications may be made without departing from the scope or spirit of the invention as defined by the following claims.

REFERENCES

Cullen, C. L., Allen, A. L., & Grahn, B. H. 1998, "Anterior chamber to frontal sinus shunt for the diversion of aqueous humor: a pilot study in four normal dogs", Veterinary Opthalmology, vol. 1, pp. 31-9.

Gal, M. *A Novel Glaucoma Drainage Valve,* 1999 [WWW document]. Proquest Digital Dissertations (visited 2002, February 28). URL http://wwwlib.umi.com/dissertations/gateway Glaucoma Research Foundation (visited 2002, Mar. 11). *Learn About Glaucoma* [WWW document]. URL http://www.glaucoma.org/

Moffett, D., Moffett, S., & Schauf, C. 1993, Human Physiology Foundations & Frontiers, $2^{nd}$ edn, Mosby, St. Louis.

U.S. Pat. Nos. 6,142,969 and 6,007,510 to Nigam. (Anamed, Inc.).

U.S. Pat. Nos. 5,454,796 and Des. 356,867 to Krupin (Hood Laboratories).

We claim:

1. A shunt for implantation between the anterior chamber of the eye and the epithelial-lined space through the frontal sinus bone of a patient for the treatment of glaucoma, comprising:
   a tube having a length sufficient to span the distance between the anterior chamber of the eye and the epithelial-lined space of the patient, the tube having an open anterior chamber end and a closed epithelial-lined space end;
   a seal device associated with the tube between the anterior chamber and epithelial-lined space ends, for sealing a hole in the frontal sinus bone, and for anchoring the tube against movement from the frontal sinus bone;
   a fluid pressure openable valve in the tube, the valve being located at or near the epithelial-lined space end of the tube such that when implemented the valve is within the epithelial-lined space, allowing for controlled flow of aqueous humor through the tube, the valve including a longitudinal slit in the tube; and
   one or more ligature devices around the tube overlying or adjacent the slit wherein at least one ligature device overlies the slit so that adjustment of the one or more ligature devices adjusts fluid flow through the valve, the one or more ligature devices tighten the slit allowing less fluid to escape from the tube and drain from the anterior chamber.

2. The shunt of claim 1, wherein the epithelial-lined space is the frontal sinus, and the closed end of the tube is thus the frontal sinus end.

3. The shunt of claim 2, further comprising a reservoir located at the closed frontal sinus end of the tube, said reservoir having a side wall forming one or more apertures through which fluid can flow from the tube, and wherein the pressure openable valve is located in the reservoir.

4. The shunt of claim 1, wherein the seal device comprises a widened portion of the tube, or a pliable spool-shaped plug fixed to the tube and through which the tube is threaded, said plug having upper and lower pliable flanges which seal on either side of the hole in the frontal sinus bone and which prevent movement of the plug relative to the frontal sinus bone, the upper flange being anterior chamber facing and being sufficiently pliable to be slid through the hole in the frontal sinus bone.

5. The shunt of claim 1, wherein the seal device or plug bends the tube through an angle sufficient to prevent kinking of the tube as it is implanted between the anterior chamber and the frontal sinus.

6. The shunt of claim 5, wherein the seal device or plug bends the tube through an angle of between 80 and 100°.

7. A shunt for implantation between the anterior chamber of the eye and an epithelial-lined space of a patient for the treatment of glaucoma, comprising:
   a tube having a length sufficient to span the distance between the anterior chamber of the eye and the epithelial-lined space of the patient, the tube having an open anterior chamber end and an epithelial-lined space end;
   a seal device associated with the tube between the anterior chamber and epithelial-lined space ends to seal and anchor the tube against movement once implanted;
   an adjustable valve in the tube to control flow of aqueous humor through the tube when implanted, the valve including a longitudinal slit in the tube; and
   a plurality of ligature devices around the tube at the slit, at least one of the ligature devices overlying the slit such that adjustment of the at least one of the ligature devices adjusts fluid flow through the valve.

8. The shunt of claim 7, wherein the valve is adjustable to open and close to maintain a desired intraocular pressure for the patient.

9. The shunt of claim 8, wherein the tube has a length sufficient to span the distance between the anterior chamber and the epithelial-lined space selected from the maxillary sinus, nasal sinus, respiratory sinus or space, subdural space or meningeal cavity.

10. The shunt of claim 9, wherein the valve is located at or near the epithelial-lined space end of the tube.

11. The shunt of claim 10, wherein the epithelial-lined space is the frontal sinus, and the epithelial-lined space end of the tube is thus the frontal sinus end.

12. The shunt of claim 11, wherein the valve is fluid pressure openable.

13. The shunt of claim 12, wherein the frontal sinus end of the tube is closed.

14. The shunt of claim 11, wherein the shunt further comprises a reservoir located at the frontal sinus end of the tube, said reservoir having a side wall forming one or more apertures through which fluid can flow from the tube, and wherein the valve is located in the reservoir.

15. The shunt of claim 11, wherein the seal device comprises a widened portion of the tube, or a pliable spool-shaped plug fixed to the tube and through which the tube is threaded, said plug having upper and lower pliable flanges which seal on either side of a hole in the frontal sinus bone and which prevent movement of the plug relative to the frontal sinus bone, the upper flange being anterior chamber facing and being sufficiently pliable to be slid through the hole in the frontal sinus bone.

16. The shunt of claim 15, wherein the seal device or the plug bends the tube through an angle sufficient to prevent kinking of the tube as it is implanted between the anterior chamber and the frontal sinus.

17. The shunt of claim 16, wherein the seal device or the plug bends the tube through an angle of between 80 and 100°.

18. A shunt for implantation between the anterior chamber of the eye and the frontal sinus of a patient for the treatment of glaucoma, comprising:
   a tube having a length sufficient to span the distance between the anterior chamber of the eye and the frontal sinus of the patient, the tube having a tube end and a valved frontal sinus end;
   a seal component on the tube spaced from the frontal sinus end to hold the tube in place in the frontal sinus;
   a slit extending longitudinally in the tube and located at the frontal sinus end, allowing for flow of aqueous humor through the tube when implanted; and
   a plurality of ligature devices around the tube at the slit to wherein at least one ligature device overlies the slit control flow through the slit.

19. The shunt of claim 18, wherein the seal component bends the tube to prevent kinking of the tube as it is implanted between the anterior chamber and the frontal sinus.

20. The shunt of claim 18, wherein the tube is formed of silicone.

21. The shunt of claim 18, wherein the tube has an internal diameter of between 0.25 and 0.64 mm.

22. The shunt of claim 18, wherein the ligature devices are mounted circumferentially around a longitudinal axis of the slit and snug enough to slightly indent the tube without disturbing an orientation of the slit.

23. The shunt of claim 18, wherein the ligature devices are formed of a biocompatible material.

24. The shunt of claim 18, wherein the ligature devices are selected from the group consisting of circumferential sutures, metal C-shaped clamps, plastic round O-rings, silicone round O-rings, and rubber round O-rings.

25. A method of treating glaucoma in a patient, comprising:
   forming a hole from the exterior into the epithelial-lined space of the patient;
   surgically implanting through the hole, between the anterior chamber and the epithelial-lined space, a shunt as defined in claim 1; and
   draining aqueous humor from the anterior chamber through the shunt to the epithelial-lined space.

26. A method of treating glaucoma in a patient, comprising:
   forming a hole from the exterior into the epithelial-lined space of the patient;
   surgically implanting through the hole, between the anterior chamber and the epithelial-lined space, a shunt as defined in claim 7; and
   draining aqueous humor from the anterior chamber through the shunt to the epithelial-lined space.

27. A method of treating glaucoma in a patient, comprising:
   forming a hole from the exterior into the epithelial-lined space of the patient;
   surgically implanting through the hole, between the anterior chamber and the epithelial-lined space, a shunt as defined in claim 18; and
   draining aqueous humor from the anterior chamber through the shunt to the epithelial-lined space.

* * * * *

UNITED STATES PATENT AND TRADEMARK OFFICE
CERTIFICATE OF CORRECTION

| | | |
|---|---|---|
| PATENT NO. | : 7,947,008 B2 | Page 1 of 1 |
| APPLICATION NO. | : 12/190211 | |
| DATED | : May 24, 2011 | |
| INVENTOR(S) | : Grahn et al. | |

It is certified that error appears in the above-identified patent and that said Letters Patent is hereby corrected as shown below:

Column 11

Claim 18, lines 40-42, delete "to wherein at least one ligature device overlies the slit" and replace with -- wherein at least one ligature device overlies the slit to --.

Signed and Sealed this

Twentieth Day of September, 2011

David J. Kappos
*Director of the United States Patent and Trademark Office*